United States Patent [19]

Fazio

[11] Patent Number: 4,661,633
[45] Date of Patent: Apr. 28, 1987

[54] METHOD FOR PREPARING QUATERNARY AMMONIUM SALTS

[75] Inventor: Michael J. Fazio, Midland, Mich.

[73] Assignee: The Dow Chemical Company, Midland, Mich.

[21] Appl. No.: 798,503

[22] Filed: Nov. 15, 1985

[51] Int. Cl.[4] ...................... C07C 85/00; C07C 95/08; C07C 97/10
[52] U.S. Cl. ..................................................... 564/286
[58] Field of Search ......................................... 564/286

[56] References Cited

U.S. PATENT DOCUMENTS

| | | | |
|---|---|---|---|
| 2,416,552 | 2/1947 | Valko et al. | 548/34 |
| 3,505,297 | 4/1970 | Sheetz et al. | 564/286 |
| 4,014,880 | 3/1977 | Dowd et al. | 260/251 |
| 4,086,273 | 4/1978 | Berazosky et al. | 260/561 |
| 4,086,274 | 4/1978 | Kaiser et al. | 260/561 |
| 4,251,459 | 2/1981 | Bargeron et al. | 564/215 |
| 4,326,067 | 4/1982 | Fazio | 548/347 |

FOREIGN PATENT DOCUMENTS 1363299  8/1974  United Kingdom ................ 564/282

OTHER PUBLICATIONS

Chemical Abstracts, vol. 82, 1975, 3767j.
Chemical Abstracts, vol. 58, 1963, No. 12805.
"Oxazoline Ring-Opening" by Edward M. Fry, Journal of Organic Chemistry, No. 15, p. 802 (1950).
"2-Aryl-4-Methyl-4-Chlorocarbonyl-Oxymethyl-2-Oxazolines, Chemical Reactivity and Infra-Red Spectra" by Rosnati & Misiti, Tetrahedron, 1960, vol. 9, pp. 175-182.
"Dow's New Award-Winning Intermediate Developmental 2-Ethyl-2-Oxazoline XAS-1454" by Dow Chemical.
"Recent Syntheses and Reactions of Cyclic Imidic Esters" by Dr. W. Seeliger, et al., Angew. Chem. Internat. Edit., vol. 5 (1966), No. 10.
Reprint from Chemical Reviews, 71, Oct. 1971, pp. 483–505 entitled "Oxazolines. Their Preparation, Reactions, and Applications" by Frump.

Primary Examiner—Werren B. Lone

[57] ABSTRACT

The specification discloses a method for preparing quaternary ammonium salts by reacting a tertiary amine salt with a 2-oxazoline or 2-oxazine compound.

16 Claims, No Drawings

METHOD FOR PREPARING QUATERNARY AMMONIUM SALTS

BACKGROUND OF THE INVENTION

The present invention relates to the preparation of quaternary ammonium salts. These are generally prepared by the alkylation of tertiary amines with alkyl halides, sulfonates or sulfates according to the following reaction.

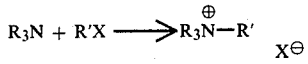

where $X = Cl, Br, I, R''SO_4^-, R''SO_3$

These reactions are limited by the availability of the alkylating agents and in the counter ion which is generated. For example, alkyl phosphates are not readily available, making it difficult to produce a quaternary ammonium phosphate.

Another method for producing quaternary ammonium sulfates involves the reaction of tertiary amines with ethylenimine in the presence of acid. This reaction results in the following type of quaternary ammonium compound:

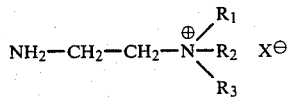

The counter ion "$X^-$" can be varied as a function of the acid used. These types of quaternary ammonium compounds are useful as antistatic agents and in the dying of acrylic fabrics.

SUMMARY OF THE INVENTION

The present invention is a method for preparing quaternary ammonium compounds by reacting a tertiary amine salt with a 2-oxazoline or 2-oxazine compound of the following formula:

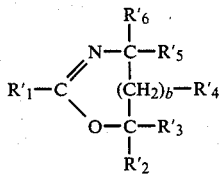

where
b is zero for oxazoline and one for oxazine; and
$R'_1$-$R'_6$ are the same or different H, alkyl or aryl substituents which will not react with, compete with or sterically interfere with the tertiary amine salt in its ring opening reaction with the oxazoline or oxazine.

DESCRIPTION OF THE PREFERRED EMBODIMENTS

The primary reaction of the present invention yields a first type of quat and is basically summarized as follows:

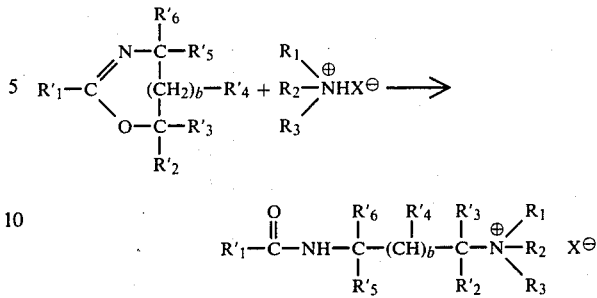

where
$R'_{(1-6)} =$ H, alkyl, aryl, with $R'_{(2-6)}$ being most preferably H;
$R_1, R_2, R_3 =$ alkyl, aryl;
b = zero for oxazoline and one for oxazine;
$X = Cl, Br, I, HSO_4, H_2PO_4$, etc.

Acid hydrolysis of the amide function of the first type of quat then yields a second type quat and acid by product as follows:

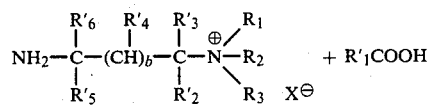

The 2-oxazoline and 2-oxazine compounds used in the present invention are generally known compounds. Methods for their synthesis are discussed in Frump, Chemical Reviews, LXXI, No. 5 (1971), pp. 483–505 at p. 486, in Seeliger et al., Angew. Chemische (International edition) V, No. 10, pp. 875–888 (1966), and in U.S. Pat. No. 4,203,900, which references are hereby incorporated by reference.

2-oxozoline compounds are more readily obtainable than 2-oxazine compounds. Hence in most commercial applications, "b" in the formula above will be zero. Examples of 2-oxazolines which can be used in the invention include 2-ethyloxazoline, 2-isopropenyloxazoline, 2-methyloxazoline, 2,5-dimethyloxazoline, 2-undecyloxazoline and 2-phenyloxazoline.

The $R'_{(1-6)}$ on the 2-oxazoline or 2-oxazine used in this process comprises a hydrogen atom, an alkyl or aryl group. $R'_{(1-6)}$ can be the same or different. $R'_{(2-6)}$ are preferably hydrogen where $R'_1$ is preferably an alkyl or aryl group. Of course where "b"=zero, there will be no $R'_4$. Examples of $R'_{(1-6)}$ substituents include hydrogen, methyl, ethyl, undecyl, stearyl, phenyl, benzyl, hydroxyethyl, and p-nitrophenyl groups.

The only limitation on $R'_{(1-6)}$ is that it must not compete to any significant degree with the tertiary amine salt for opening the oxazoline ring, must not significantly react with the amine and must not sterically hinder the ring opening reaction. The foregoing limitations are to be considered in the context of a specific reaction system and specific ingredients which can be added to the system to effectively minimize the occurrence of the foregoing undesirable effects.

The $R_1$, $R_2$ and $R_3$ components of the tertiary amine salts used in the present invention can be the same or different alkyl or aryl groups. Basically, the only limitation on the particular alkyl or aryl groups is that, as above for $R'_{(1-6)}$, they must not interfere with or hinder the oxazoline ring opening reaction. The alkyl and aryl groups mentioned above in connection with $R'_{(1-6)}$ are also operable examples for $R_1$, $R_2$ and $R_3$.

The "$X^-$" counter ion of the tertiary amine salt can be any counter ion available in an acid. The examples for "$X^-$" given above are by no means limiting. One skilled in the art can tailor the reaction by choosing any of the broad number of counter ions available. The only limitation on the counter ion is that it must not significantly compete with the tertiary amine for opening the oxazoline ring.

The tertiary amine is reacted with an appropriate acid to create the desired tertiary amine salt. Examples of tertiary amines which can be used to create the tertiary amine salts for this reaction include tributylamine, triethylamine, triethanolamine, pyridine and dimethylaniline.

The use of free amines can help control selectivity of the reaction, i.e., insure that the primary reaction is between the tertiary amine salt and the oxazoline ring. For example, where the $R'_1$ substituent is vinyl or isopropenyl, the amine or another oxazoline will tend to add at the double bond. The presence of free amine reduces the amount of double bond addition. As an alternative to adding free amine, some inorganic base such as sodium hydroxide can be used to generate free amine during the reaction.

Vinyl polymerization inhibitors may be employed where the $R'$ substituent includes a vinyl group. Examples of vinyl polymerization inhibitors include phenothiazine or MEHQ.

The reaction is generally carried out in a polar solvent such as isopropanol, ethanol, methanol or acetonitrile. The reaction must be carried out under anhydrous conditions to avoid hydrolyzing the oxazoline ring. The stoichiometry for the reaction is basically 1:1, but an excess of the amine salt can be used.

The reaction is preferably carried out at between 100°–125° C. Higher or lower temperatures may be appropriate for specific reactions.

EXAMPLE 1

The production of N-(2-propionamidoethyl)-N,N,N-trimethyl ammonium chloride is illustrated in Example 1. Ethyloxazoline (3.04 g., 0.03 mol), trimethylamine hydrochloride (2.74 g., 0.03 mol) and 20 ml isopropanol were charged into a 45 ml Parr reactor, a stainless steel pressure reactor. The mixture was heated 3 hours at 100° C. The mixture was then cooled and the solvent and unreacted oxazolines stripped at reduced pressure. Crude product, 5.8 g., crystallized on standing. The product was recrystallized from acetone to yield white hygroscopic needles. Structure was assigned based on spectral data.

The foregoing reaction can be written basically as follows:

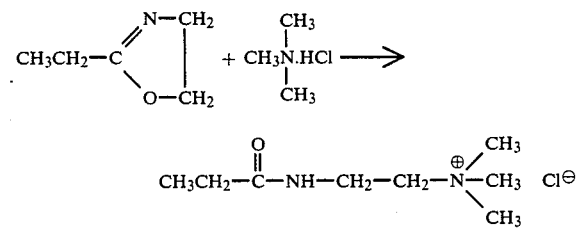

EXAMPLE 2

The production of N-(2-methacrylamidoethyl)-N,N,N-trimethyl ammonium chloride is illustrated in Example 2. Isopropenyloxazoline (2.5 g., 0.02 mol), trimethylamine hydrochloride (2.7 g., 0.03 mol), trimethylamine (0.7 g., 0.01 mol) (added to speed up rection and help control selectivity) and 15 ml isopropanol were charged into a 45 ml Parr reactor. The mixture was heated for 16 hours at 105° C. The mixture was cooled, diluted with water and stripped at reduced pressure. 6.4 grams of crude product recovered is a mixture of desired product, unreacted trimethylamine hydrochloride and some double bond addition product.

The foregoing reaction is written as follows:

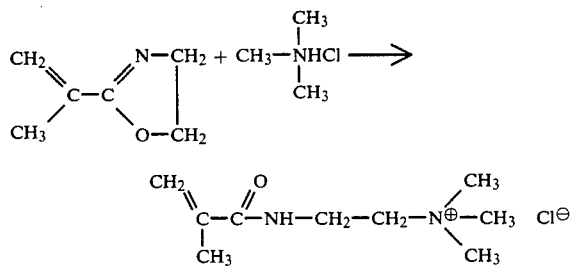

The product of Example 2 is a cationic monomer used in the preparation of polymers for water treatment, paper making, cosmetics, mineral processing and enhanced oil recovery.

The embodiments of the present invention in which an exclusive property or privilege is claimed are defined as follows:

1. A method for preparing quaternary ammonium compounds comprising:
    reacting a tertiary amine salt with a 2-oxazoline or 2-oxazine compound of the following formula:

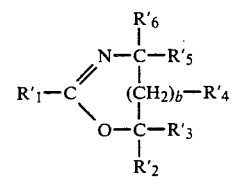

where
b is zero for oxazoline and one for oxazine; and
$R'_1$–$R'_6$ are the same or different H, alkyl or aryl substituents which will not react with, compete with or sterically interfere with the tertiary amine salt in its ring opening reaction with the oxazoline or oxazine.

2. The method of claim 1 which includes the further step of hydrolyzing the quaternary ammonium compound first obtained to obtain an alternative quaternary ammonium compound.

3. The method of claim 2 in which $R'_2$–$R'_6$ are hydrogen atoms.

4. The method of claim 1 in which $R'_2$–$R'_6$ are hydrogen atoms.

5. The method of claim 4 in which said reaction is carried out in the presence of free amine.

6. The method of claim 1 in which said reaction is carried out in the presence of free amine.

7. The method of claim 6 which includes the further step of hydrolyzing the quaternary ammonium compound first obtained to obtain an alternative quaternary ammonium compound.

8. The method of claim 7 in which $R'_2$–$R'_6$ are hydrogen atoms.

9. The method of claim 1 in which said oxazoline or oxazine comprises ethyloxazoline.

10. The method of claim 9 in which said tertiary amine salt comprises trimethylamine hydrochloride.

11. The method of claim 1 in which said oxazoline or oxazine comprises isopropenyloxazoline.

12. The method of claim 11 in which said tertiary amine salt comprises trimethylamine hydrochloride.

13. The method of claim 12 in which said reaction is carried out in the presence of free amine.

14. The method of claim 11 in which said reaction is carried out in the presence of free amine.

15. The method of claim 11 in which a vinyl polymerization inhibitor is added to the reaction system.

16. The method of claim 1 in which one of said $R'_1$–$R'_6$ substituents includes a vinyl group and a vinyl polymerization inhibitor is added to the reaction system.

* * * * *

UNITED STATES PATENT AND TRADEMARK OFFICE
CERTIFICATE OF CORRECTION

PATENT NO. : 4,661,633

DATED : April 28, 1987

INVENTOR(S) : Michael J. Fazio, Midland, Mich.

It is certified that error appears in the above-identified patent and that said Letters Patent is hereby corrected as shown below:

Column 1, formula under "Summary of the Invention", that portion of the formula reading "$(CH_2)_b$-$R'_4$"  should read -- $(CH)_b$-$R'_4$ --.

Column 2, first formula under "Description of the Preferred Embodiments", that portion of the formula reading "$(CH_2)_b$-$R'_4$ + $R_2$"  should read -- $(CH)_b$-$R'_4$ + $R_2$ --.

Column 2, line 39, "2-oxozoline" should be -- 2-oxazoline --.

Column 4, line 7, add an "a" between the "e" and "c-" to spell "reaction."

Column 4, second formula under "Example 2", that portion of the formula reading

"$(CH_2)_b$-$R'_4$"  should be -- $(CH)_b$-$R'_4$ --.

Signed and Sealed this

Twenty-sixth Day of January, 1988

Attest:

DONALD J. QUIGG

Attesting Officer     Commissioner of Patents and Trademarks